(12) United States Patent
Geebelen et al.

(10) Patent No.: US 8,702,686 B2
(45) Date of Patent: Apr. 22, 2014

(54) ADAPTABLE THERAPEUTIC, DIAGNOSTIC OR SURGICAL GUIDE

(75) Inventors: Ben Geebelen, Haasrode (BE); Roel Wirix-Speetjens, Maaseik (BE); Louis James Keppler, Strongsville, OH (US); Wilfried Vancraen, Huldenberg (BE)

(73) Assignee: Materialise NV, Leuven (BE)

( * ) Notice: Subject to any disclaimer, the term of this patent is extended or adjusted under 35 U.S.C. 154(b) by 0 days.

(21) Appl. No.: 13/395,260

(22) PCT Filed: Sep. 10, 2010

(86) PCT No.: PCT/EP2010/063330
§ 371 (c)(1),
(2), (4) Date: Mar. 9, 2012

(87) PCT Pub. No.: WO2011/029911
PCT Pub. Date: Mar. 17, 2011

(65) Prior Publication Data
US 2012/0179147 A1    Jul. 12, 2012

Related U.S. Application Data

(60) Provisional application No. 61/242,952, filed on Sep. 16, 2009.

(30) Foreign Application Priority Data

Sep. 11, 2009 (GB) .................................... 0915947.6

(51) Int. Cl.
*A61B 17/00* (2006.01)
*B23C 3/00* (2006.01)

(52) U.S. Cl.
USPC ................................................ 606/1; 409/79

(58) Field of Classification Search
None
See application file for complete search history.

(56) References Cited

U.S. PATENT DOCUMENTS

| | | |
|---|---|---|
| 2005/0113924 A1 | 5/2005 | Buttermann |
| 2008/0215153 A1 | 9/2008 | Butterman et al. |

(Continued)

FOREIGN PATENT DOCUMENTS

| | | |
|---|---|---|
| WO | WO 2005/013852 A2 | 2/2005 |
| WO | WO 2009/001083 A1 | 12/2008 |

OTHER PUBLICATIONS

International Preliminary Report on Patentability (PCT/EP2010/063330), dated Mar. 22, 2012.

(Continued)

*Primary Examiner* — Bill Thomson
*Assistant Examiner* — Scott T Luan
(74) *Attorney, Agent, or Firm* — EIP US LLP (57) ABSTRACT

The present invention relates to an adaptable therapeutic, diagnostic or surgical guide for an intra-operative adjustment of a guidance element to a pre-planned position. An advantage and innovation of the present invention is that it provides a template or guide that adapts in a controlled way to a changed intra-operative anatomical situation compared to the default planned situation. This adaption maybe purely positional but it may also include force feedback. Feedback, either visual feedback or force feedback that results in an adjustment of a guidance element is also an aspect of the present invention. For example, the feedback can contain information either about the fit of the guide or template onto a bone (in case the guide or template fits onto one bone) or about the relative position of two bones of bone fragments (e.g. ligament tension between the femur and tibia).

18 Claims, 10 Drawing Sheets

(56) References Cited

U.S. PATENT DOCUMENTS

| | | | |
|---|---|---|---|
| 2008/0221581 A1* | 9/2008 | Shoham | 606/96 |
| 2008/0243127 A1 | 10/2008 | Lang et al. | |
| 2008/0281328 A1 | 11/2008 | Lang et al. | |
| 2008/0281329 A1 | 11/2008 | Fitz et al. | |
| 2008/0281426 A1 | 11/2008 | Fitz et al. | |
| 2009/0087276 A1 | 4/2009 | Rose et al. | |
| 2009/0088753 A1 | 4/2009 | Aram et al. | |
| 2009/0088754 A1 | 4/2009 | Aker et al. | |
| 2009/0088755 A1 | 4/2009 | Aker et al. | |
| 2009/0088758 A1 | 4/2009 | Bennett | |
| 2009/0088759 A1 | 4/2009 | Aram et al. | |
| 2009/0088760 A1 | 4/2009 | Aram et al. | |
| 2009/0088761 A1 | 4/2009 | Roose et al. | |
| 2009/0088763 A1 | 4/2009 | Aram et al. | |
| 2009/0093816 A1 | 4/2009 | Roose et al. | |
| 2009/0099567 A1 | 4/2009 | Zajac | |
| 2009/0131942 A1 | 5/2009 | Aker et al. | |
| 2010/0305573 A1 | 12/2010 | Fitz et al. | |
| 2010/0305574 A1 | 12/2010 | Fitz et al. | |
| 2012/0143198 A1* | 6/2012 | Boyer et al. | 606/87 |

OTHER PUBLICATIONS

Notification of Transmittal of the International Search Report and the Written Opinion of the International Searching Authority; International Search Report; and Written Opinion in International Application No. PCT/EP2010/063330, mailed Dec. 27, 2010 (8 pages).

* cited by examiner

ADAPTABLE THERAPEUTIC, DIAGNOSTIC OR SURGICAL GUIDE

Cross-Reference to Related Applications

This application is the U.S. national stage of International Patent Application No. PCT/EP2010/063330, filed Sep. 10, 2010, which claims the benefit of United Kingdom Patent Application No. 0915947.6, filed Sep. 11, 2009 and U.S. Patent Application No. 61/242,952, filed Sep 16, 2009.

TECHNICAL FIELD OF THE INVENTION

The present invention relates to a medical, e.g. therapeutic, diagnostic or surgical guide for invasive medical treatments. It applies more particularly, but not exclusively, to a medical or surgical guide for computer aided and computer planned treatments in cases where the guide has to be adapted intra-operatively to a targeted area of a patient.

BACKGROUND OF THE INVENTION

At present, there exists an increasing number of surgical interventions that benefit from the use of medical image based patient specific surgical guides as described for example in patent applications US 2005/0203528 A1 and EP 1 486 900 A1.

Thus, surgical guides are currently produced to give a unique anatomic position which corresponds to a patient specific pre-operative surgical plan. This plan is based on images of the patient with the assumption that the patient anatomy does not vary significantly within the time, maybe months after being imaged. If the patient's anatomy on which the guide was designed changes during this waiting period, the guide will not have a unique fit.

A second limitation of using a static, image-based guide is that the images may be unclear in certain regions. This has an effect in two ways: firstly, incorrect planning based on unclear anatomic landmarks is possible, for example a cut is deeper than expected; and secondly, the resulting guide does not fit in certain regions. With the static guide models complete surface matching is often not possible. Gaps or hinges can be introduced between the guide and the patient anatomy due to imperfect image segmentation or a change in patient anatomy between the imaging date and the surgical date.

Surface hinges are most detrimental to the guide fit since they limit the remaining surface contact and the unique fit is then impossible. To compensate for possible hinges large gaps are intentionally made over these regions so that the majority of the surface can still make contact and produce a proper fit. However, with less surface contact available, the likelihood of an improper fit even increases. This improper fit can lead to incorrect surgical results since the active elements are in a different position than what was pre-operatively planned.

Often, windows are added to a guide so that the surgeon can check for gaps along the guide surface to determine the quality of the fit. This creates a compromise between fit visibility and use of a possible locking surface area. The more locking surface used to make the guide, the less visibility the surgeon has as to see if the fit is good or not.

A third limitation of the current surgical guides is that they transfer a surgical plan that is only based on the images and intraoperative visual information. However, in some interventions there are good reasons to adjust the original plan during surgery based on tangible information. The tension inequality in the ligaments of a joint (e.g. ligament balancing in knee surgery) is impossible to visualise in most situations, but it is an element considered by many surgeons.

The result is that multiple surgical acts are difficult to perform in a guided way and hence, in fact, finally rely on mental navigation once a difference from the pre-planned patient anatomy is determined. In some medical conditions, adjustable guides have been conceived to allow for some variability intra-operatively to adjust the referenced functional elements like guides for drill holes or cut planes. (U.S. Ser. No. 12/039,849) These modifications to the pre-operative planning have to be done manually by shifting or rotating active elements of the guide so that they align visually to certain anatomic structures or landmarks. It would be possible to define a range of probable surgical results based on the maximum rotation or translation of the active components. However, the exact point within the range is determined by visual references and is made manually. These adjustable guides also have the same risks as static guides in that they can be misplaced on the anatomic surface since they use a static surface contact. If this occurs, the surgeon can no longer trust any pre-operative planning since the reference position is inaccurate.

Thus, the adjustment can be needed but is problematic for the same reasons as those that affect the fit of guides, but also due to the fact that the position of the body of the patient may be quite different on the operation table compared to the time when the image scans were taken.

An alternative approach to the problem is to perform some surgical acts that need high accuracy whilst the patient is being scanned. Theoretically this gives the best guiding feedback to the surgeon, because he can see in real time what he is actually doing. However imaging for long periods during an operation, adds its own risks for the patient and the medical staff, e.g. radiation exposure.

SUMMARY OF THE INVENTION

It is an object of the present invention to provide an alternative medical e.g. therapeutic, diagnostic or surgical guide for invasive medical treatments, in particular a medical e.g. therapeutic, diagnostic or surgical guide for computer aided and computer planned treatments in cases where the guide has to be adapted intra-operatively to a targeted area of a patient.

This object is accomplished by a medical e.g. therapeutic, diagnostic or surgical guide according to the present invention. An advantage and innovation of the present invention is that it provides a template or guide that adapts in a controlled way to a changed intra-operative anatomical situation compared to the default planned situation. The adaptation can be used to provide feedback to the surgeon as to the medical situation intraoperatively or preoperatively, but also be used to overcome manufacturing tolerances. This adaption maybe purely positional but it may also include force feedback. Feedback, either visual feedback or force feedback, that results in an adjustment of a guidance element is also an aspect of the present invention. For example, the feedback can contain information either about the fit of the guide or template onto a bone (in case the guide or template fits onto one bone) or about the relative position of two bones or bone fragments (e.g. ligament tension between the femur and tibia).

Accordingly, the present invention provides a medical e.g. therapeutic, diagnostic or surgical guide having a guidance element that allows for an intra-operative positioning of the guide or of a guidance element to a pre-planned position, comprising:

a first reference element,
  at least one contact element elastically mounted with respect to the first reference element by means of at least one elastic element,
wherein the guidance element is attached to the first reference element, a deformation of the at least one elastic element corresponding to the intra-operative position of the at least one contact element. The position of the elastic element that corresponds to the intra-operative position of the at least one contact element or the position of the contact element itself provides at least a visual feedback. The feedback may be provided by visual feedback means, e.g. markings, shapes, colours etc. which indicate the intra-operative position of the contact elements either directly or indirectly. The feedback may be a simple right/wrong indication or may include a graded indication.

In one particular embodiment, the guidance element of the therapeutic diagnostic or surgical guide is adaptively attached to the first reference element, such that the adaptation of the guidance element is achieved by the deformation of the at least one elastic element which allows a correspondence to an intra-operative position of the at least one contact element.

In an embodiment, the present invention proposes a new design of medical e.g. therapeutic, diagnostic or surgical guides that is based on using a medical image based mechanical guiding system that accurately fits for a targeted area of the patient and allows precise targeting and control of surgical interventions.

A medical e.g. therapeutic, diagnostic or surgical guide according to the present invention acts as the basis for a well defined and adaptable positioning of medical e.g. therapeutic, diagnostic or surgical guides or functional guiding elements. The guiding elements allow one to execute an invasive therapeutic, diagnostic, or surgical act (such as insertion of a biopsy needle), placement of reference pins, drilling of holes, or surgical cuts (such as making osteotomy cuts) accurately according to a predefined surgical plan made with 3D-imaging technology such as: optical, CT, MRI, PET, or Ultrasound imaging. In some situations the functional guiding element may even comprise or interface with an electronic surgical navigation system.

In the current invention a first reference element is provided such as a frame or substrate to which other elements are attached. The first reference element does not need to be patient-specific, for example the first reference element any be of any suitable shape, and the distance(s) to contact element(s) is set such that the contacting parts of the contact elements are located in a patient-specific way, i.e. their envelope defines a negative shape of a body part. The contact points may be multiple contact points or the contact elements may have an envelope, e.g. surface that is shaped in a patient specific way, i.e. has the negative shape of a part of the patient's anatomy.

Alternatively, the first reference element can be given a patient-specific shape, and the one or more contact elements are distanced at a predefined distance from the reference element so that the one or more contact elements have contact parts that are also located at positions, i.e. one an envelope that are patient-specific due to the shape of the reference element.

Yet another possibility is that neither the first reference element nor the contact elements are given a patient specific form, but the feedback means, e.g. the markings on the elastic means are located at patient specific points. Thus, once the guide is applied the relationship between the patient specific markings and the individual positions of the elastic elements provides the visual feedback to the physician.

The present invention also includes in one embodiment of the present invention that a second reference element is provided. The second reference element is preferably patient specific, i.e. has the negative shape of a part of the patient's anatomy.

In any case, the contact elements, which comprise one or more of pre-defined outer surfaces or multiple point-contacts which define a surface or envelope that is patient specific, i.e. has the negative shape of a part of the patient's anatomy, are preferably made in accordance with the pre-operative plan for the surgical intervention.

The contact element can comprise one surface or a point-contact which is intended to be in contact with the targeted area of the patient, the contact element mirroring the surface of the targeted area of the patient. For example, it can be distanced to the reference surface at a predefined distance. The contact element can comprise more than one surface or can be multiple point contacts like in a multi-point or multi-surface arrangement, the position of contact points or surfaces being patient specific, i.e. define a surface or envelope that is the negative form of a body part. The contact parts of the contact element can move relative to the first reference element surface. The surface of the contact element contacts the patient's anatomy and fits to or conforms to that shape. The relative movement between the conformed contact surface(s) or contact point(s) and a fixed outer reference surface can allow the user to compare the predicted surface fit with the actual patient anatomy. Gaps would be seen as the contact surface(s) or point(s) further away from the reference outer surface while so called "hinges" would bring the two surfaces closer to each other. This immediately provides the advantage that hinges do not necessarily void the entire guide fit since the contacting surface is comprised of several independent elements. A correct fit could be determined by a percentage of the inner contact element surface staying within a consistent distance from the outer reference surface.

In embodiments of the present invention, the outer reference element surface and the inner contact surfaces are attached to each other and their relation measured using elastically deformable elements. These physical elements can either be used to directly display the fit data or they can be linked to other measuring devices such as micrometers or strain gauges, for example, to give a digital readout. Based on this readout, the physician can adjust the position of the guidance element to achieve the optimal surface match or discard the guide if an improper fit is determined. This greatly reduces the risk of a surgical guide being used in an improper position and allows the surgeon to take into account the contact element surfaces of the surgical guide not seen along the outer border or windows.

Spring loaded, elastic deformable guidance element structures can also be used. These deformable guidance elements may be activated by the movement of the contact elements such that the position of the guidance elements depends on the intra-operative position of the contact elements. The movement of the guidance elements may be controlled by a transducer element. These deformable guidance elements may provide a clamping force onto an anatomic region. By applying a force to certain curvatures, the guide can lock more securely to the targeted area of the patient.

In a preferred embodiment of the present invention the first reference element consists of a rigid structure with adjustable contact elements adapted to fit the specific targeted area of a single patient. In this way, the first reference element and contact elements optionally in co-operation with a second reference element durably reflect the computer-aided plan for the surgical intervention.

In another preferred embodiment of the present invention the medical e.g. therapeutic, diagnostic or surgical guide comprises at least two contact elements.

Advantageously, by using at least two contact elements like multiple point contact elements the areas of the patient which show an improper fit can be better defined and are thus better to identify by the surgeon while those areas with a matching fit are increased.

Preferably, the at least one elastic element is chosen from the group consisting of a strain gauge, a spring, a deformable rubber or foam, and an inflatable cushion.

The first goal of the elastic element is to ensure that the surface or contact point of the contact element remains in contact with the anatomic region of the patient. The elastic elements can also provide an indicator function, i.e. they can be used to directly display the fit data (i.e. for use in optical navigation). Alternatively, they can be operatively connected to other measuring devices—such as is the case when strain gauges are used—to give an analog or digital readout. Based on this readout, the physician can adjust the position of the guide to achieve the optimal surface match or discard the guide if an improper fit is determined. This greatly reduces the risk of a guide being used in an improper position and allows the surgeon to take into account the contact surfaces of the guide not seen along the outer border or windows.

In another preferred embodiment of the present invention the surgical guide comprises a transducer element attached to the at least one elastic element and in operative contact with the guidance element.

By directly linking the possible deformation of the elastic element to movement of the functional guidance element via the transducer element there is a means provided for an auto-adjustment of the guidance element to the changes of the patient area without manual handling by the surgeon.

The transducer element can comprise an actual transducer part and a part which defines the transduction function to the functional guidance element. The actual transducing part is provided so that it can move in relation to the moving surface of the contact element. This motion is then the input for the transduction function part. The distance information by the transducer can also be converted to a digital signal for analysis and guide adaptation.

The transduction function should relate the final position of the moving surface of the contact element to the resulting planning position of the functional guidance element. While it can be represented as a physical curve for conceptual demonstration, this can also be provided using such physical elements such as gears, hinges, screws etc. or by using an electronic (digital) function which then gives a resulting position of the functional guidance element.

Hence the present invention provides a medical e.g. therapeutic, diagnostic or surgical template or guide that provides feedback (visual, position or force) comprising:

at least one reference element (this can be a patient-specific or not, is typically a rigid region of the template);

at least one flexible, patient-specific element, i.e. a contact element typically a point or surface and made flexible by means of an elastic element; and an indicator or actuator providing visual patient specific feedback or enabling the force feedback relating to the position, of the flexible, contact element to the reference element.

In some embodiments, fit information is obtained when both the reference and flexible element are positioned onto the same part of the anatomy of the patient. In some embodiments, when the reference element is placed onto a part of the anatomy of the patient, e.g. a bone or a bone fragment, and the flexible element is placed onto another part of the anatomy of the patient, e.g. another bone or bone fragment, information regarding the position between bones is obtained (e.g. as determined by ligament tension).

The adaptable surgical guide according to the present invention is preferably used for medical treatments, especially in cases where the surgical guide is intra-operatively adapted to the targeted area of a patient. Such pre-planned surgical interventions benefit the most where intra-operative adjustment of the guidance elements is needed to reflect the changes of the fit of the patient specific prefabricated guide.

Other features and advantages of the present invention will become apparent from the following detailed description, taken in conjunction with the accompanying drawings, which illustrate, by way of example, the principles of the invention.

DESCRIPTION OF THE ILLUSTRATIVE EMBODIMENTS

The present invention will be described with respect to particular embodiments and with reference to certain drawings but the invention is not limited thereto but only by the claims. The drawings described are only schematic and are non-limiting.

Figure 1A:
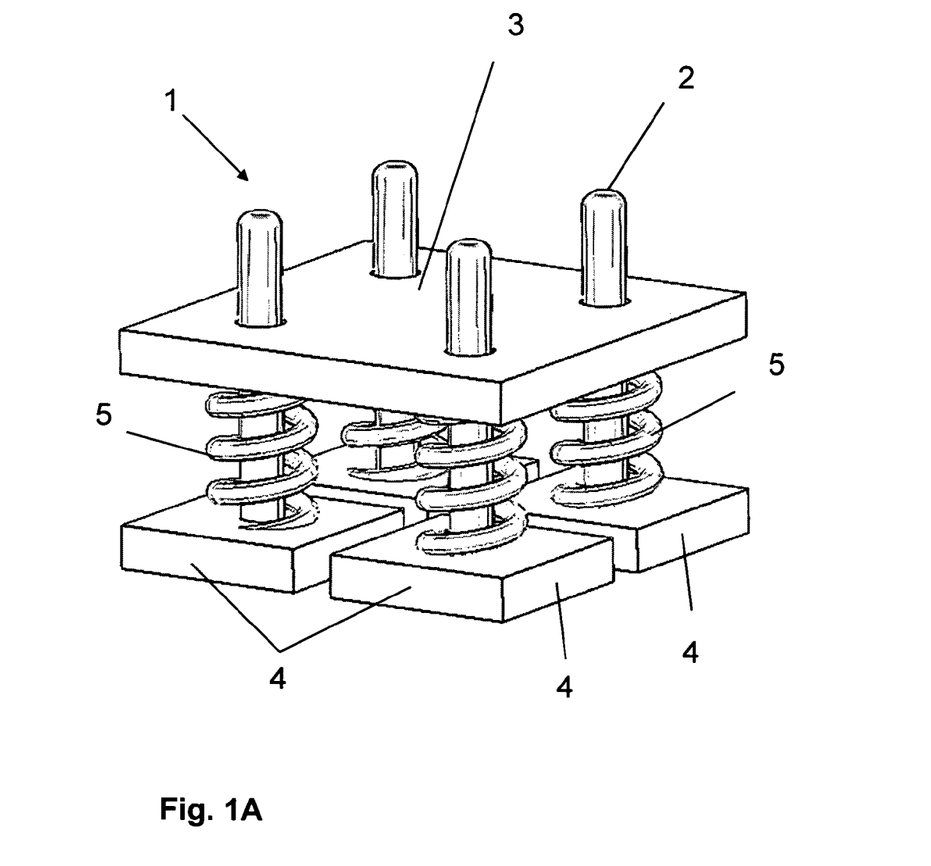
FIGS. 1A-C are schematic views of parts of a guide that can be used with the present invention.

FIG. 1A is a schematic view of a feedback device for use in a surgical guide 1 according to the present invention. For a better understanding of the general working principle, the elements of the inventive guide are shown in a very simplified schematic manner.

An adaptable surgical guide 1 for an intra-operative adjustment of a contact element to a pre-planned position comprises the feedback device that has a first reference element 3 shown as a plate structure. The feedback device is shown to be a cut plane defined by the surfaces of the individual members attached to the contact elements 4. Four contact elements 4 are connected to the reference plate 3 via individual elastic elements 5 provided between the reference element 3 and the contact elements 4. The contact elements are movable thanks to the elastic elements. The position of the contact elements can be seen from the position of indicators 2 which allow visualisation of a later correspondence to the intra-operative position of the contact elements.

Figure 1B:
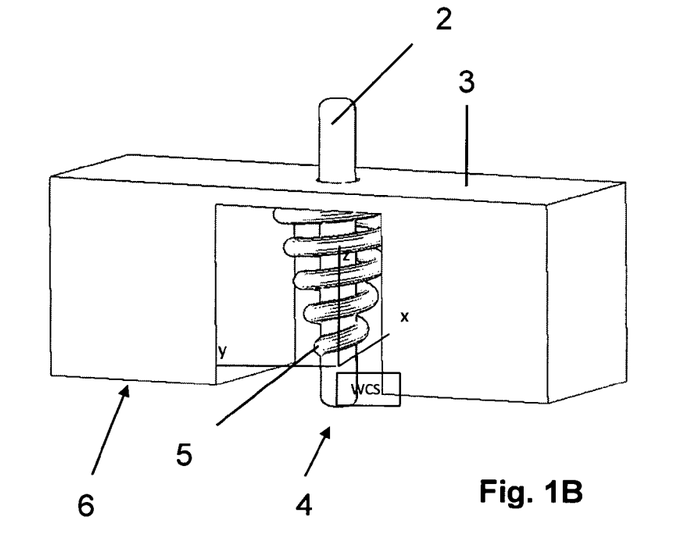

FIG. 1B is a schematic view of another feedback device for use in a surgical guide 1 according to the present invention similar to that shown in FIG. 1A except that the contact element 4 is recessed. The indicator 2 extends beyond the outer surface of reference element 3 and indicates the position of the contact element 4 that is elastically mounted with respect to the spring 5. A second reference surface 6 is provided, e.g. that can control or restrict the position of the contact element 4. It is a particular aspect of the present invention that the second reference surface 6 which acts as a second reference element is preferably patient specific in shape or form, i.e. has the negative shape of a part of the patient's anatomy. The second reference element can be used to allow a good visual feedback as to whether the guide is located correctly.

Figure 1C:
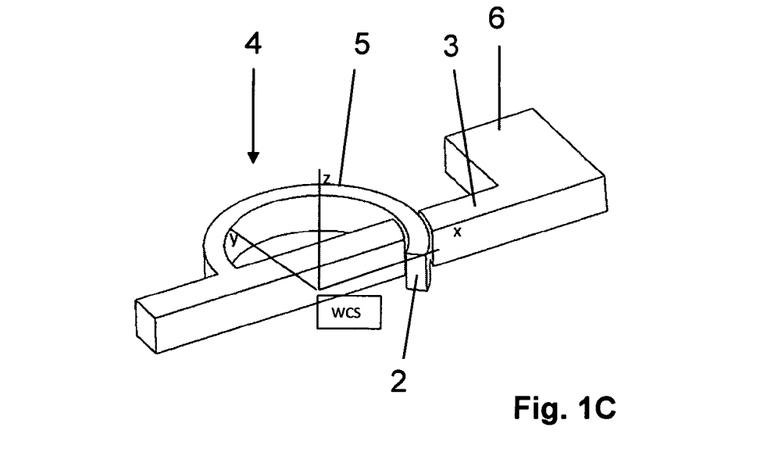

FIG. 1C is a schematic view of yet another feedback device for use in a surgical guide 1 according to the present invention similar to that shown in FIG. 1A except that the elastic element is a curved spring 5 whose deformation moves the indicator 2 with respect to the outer surface of the first reference element 3. The contact element 4, in the form of a point or surface, is provided by a section of the curved spring on the side of the reference element 3 remote from the indicator 2. Optionally a second reference surface 6 is provided, e.g. that can control or restrict the position of the contact element 4.

Figure 1D:
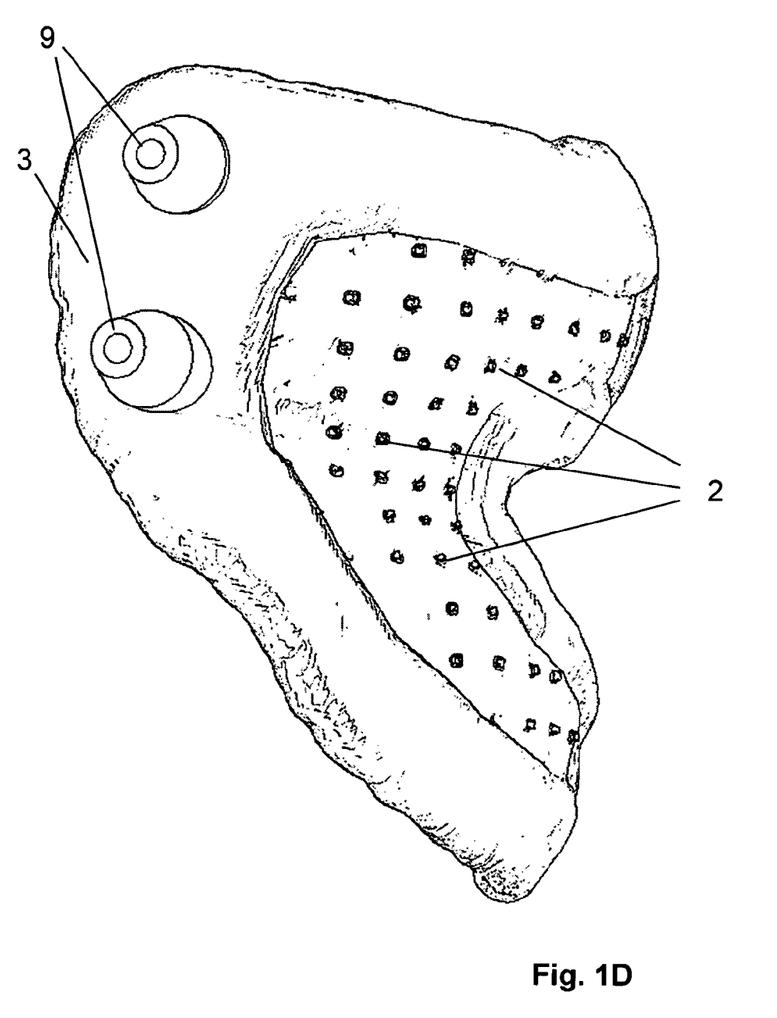
FIGS. 1D and E show a first embodiment of an adaptable surgical guide according to the present invention.
Figure 1E:
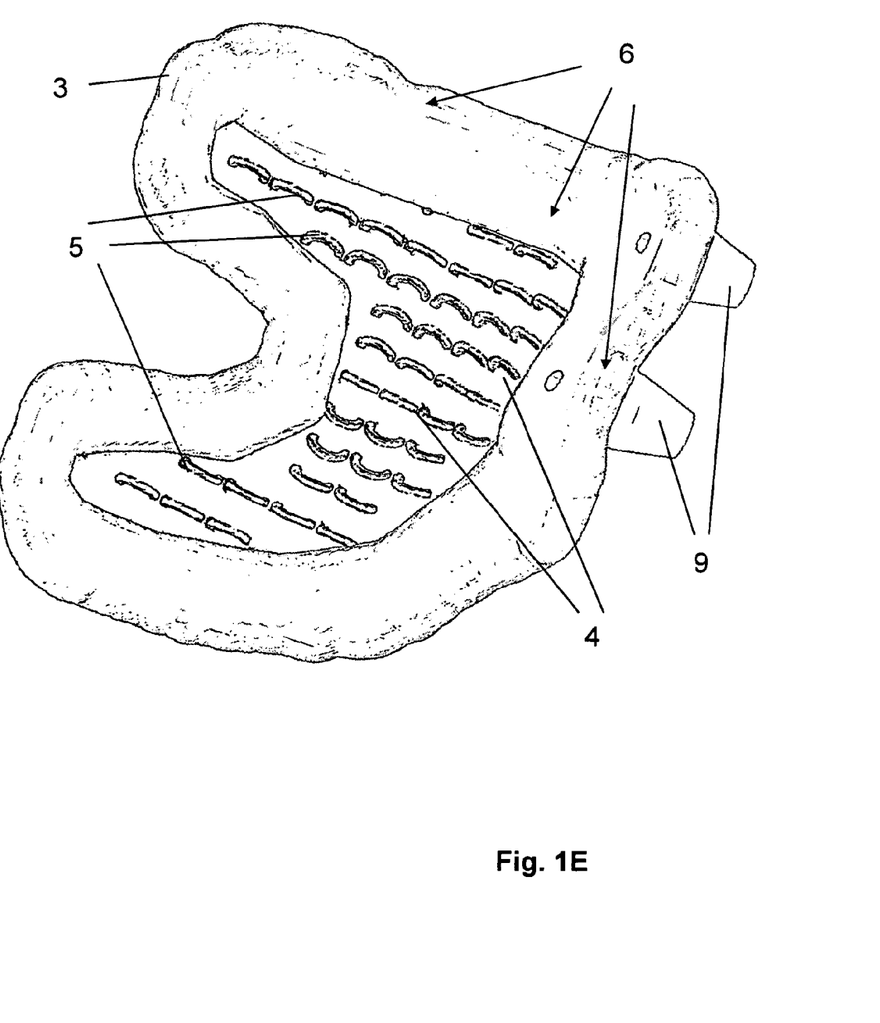

How the above feedback devices can be used in a medical e.g. therapeutic, diagnostic or surgical guide 1 will be described with reference to FIGS. 1D and 1E. FIG. 1D shows a medical e.g. therapeutic, diagnostic or surgical guide 1 that has a reference element 3 that has a specific shape that is the mirror image of a part of a patient, e.g. of a bone such as part of a femur. The reference element 3 can be made by any of the methods described later that use layered manufacture, additive manufacture or rapid prototyping, for example. The reference element 3 may be constructed by such methods based on a suitable image, e.g. a CT-Scan, an MRI-scan, an ultrasound scan, a PET-scan, etc. On the outer surface of the reference element 3 indicators 2 can be seen that are distributed over the surface. These indicators 2 are operatively connected to elastic elements 5, see FIG. 1E, which shows the inside surface of the guide 1. The elastic elements can be any of the elastic elements shown in FIGS. 1A to C. For example, here they are curved springs similar to those shown in FIG. 1C. The guide also has a second reference element in the form of a patient specific surface 6, i.e. has the negative shape of a part of the patient's anatomy. This patient-specific surface mirrors the shape of a part of the anatomy of the patient. When the guide is in the correct position this is indicated by the indicators 2. The curved springs 5 also form contact points or surfaces 4 such that when the guide is applied to the patient the curved springs will interfere more or less with the patient anatomy depending upon the exactness of the positioning of the guide 1, i.e. whether the second reference element, i.e. the surface 6 is in the correct position. Errors in the positioning will appear as movements of the indicators 2, hence these provide an optical feedback. These indicators 2 will protrude through the reference element 3 more or less depending on the goodness of fit. The indicators 2 may have coloured bands or other markings on them to allow a better visualisation of the degree to which they have penetrated through the reference element. By altering the position of the guide 1, the surgeon may search for a best fit. The guide 1 also has one or more guidance elements 9, here shown as guide elements such as drill guides. However the guidance element 9 could be any type of guide for invasive operations such as a cutting guide for surgical interventions.

Figure 2:
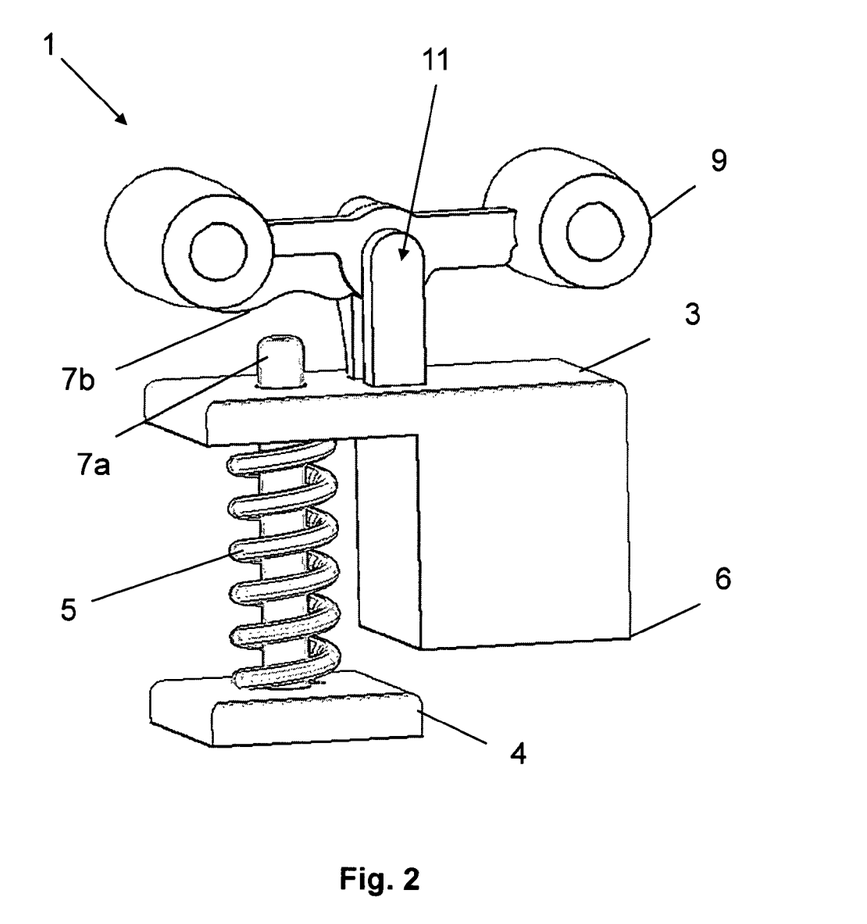
FIG. 2 is a schematic view of a second embodiment of an adaptable surgical guide according to the present invention.

FIG. 2 is a schematic view of another feedback device for use with a surgical guide 1 according to the present invention in a second embodiment. Again, the elements of the inventive guide are shown in a very simplified schematic manner for a better understanding of the general working principle. The reference element 3 is depicted as a plate to which a spring as elastic element 5 is attached. At the corresponding end of the spring 5 a contact element 4 is placed which is also depicted as a plate. The reference element carries a hinge structure including a pivot 11 to which the functional guidance element 9 is attached so that it can be moved (in an accurate path) by the corresponding movement of a transducer element 7 to the movement of the contact element 4. The guidance element 9 is shown as guide element such as a drill guide with two holes for the guidance of drills. However the guidance element 9 could be any type of guide for invasive operations such as a cutting guide for surgical interventions. The transducer element 7 comprises two different parts 7a and 7b which are intended to translate the adjustment movement of the contact element 4 in respect to the reference element 3 and hence to functional guidance element 9. Reference number 7a denominates an actuator part and reference number 7b denominates the transducer part which defines the transduction function to the functional guidance element 9. As shown, the transducing function is depicted as an arcuate path or curved trace of the guidance element 9 for conceptual demonstration but it is also possible to provide other paths or trajectories using other physical elements such as gears, hinges, screws etc. or by using an electronic function which then gives a resulting position of the functional guidance element 9. Another (second) reference element 6 can be positioned, for example at a fixed distance to the first reference element 3. For example, the fixed distance describes the distance the contact element should have in respect to the first reference element 3 according to the predefined planning of the surgery. Like that, deviations of the contact element 4 from the match with the second reference element 6 can easily be observed. Due to the fact that the guidance element 9 is actuated by the position of the contact element, this embodiment provides more than just a visual feedback. In this case the feedback is to provide the intra-operative position of the guidance element 9 derived from the intra-operative anatomical position of anatomical elements of the patient.

In an alternative embodiment of the present invention the functional guidance element can be locked in its final (intra-operative) position by means of any suitable locking means, e.g. that prevents rotation about the pivot.

Figure 3:
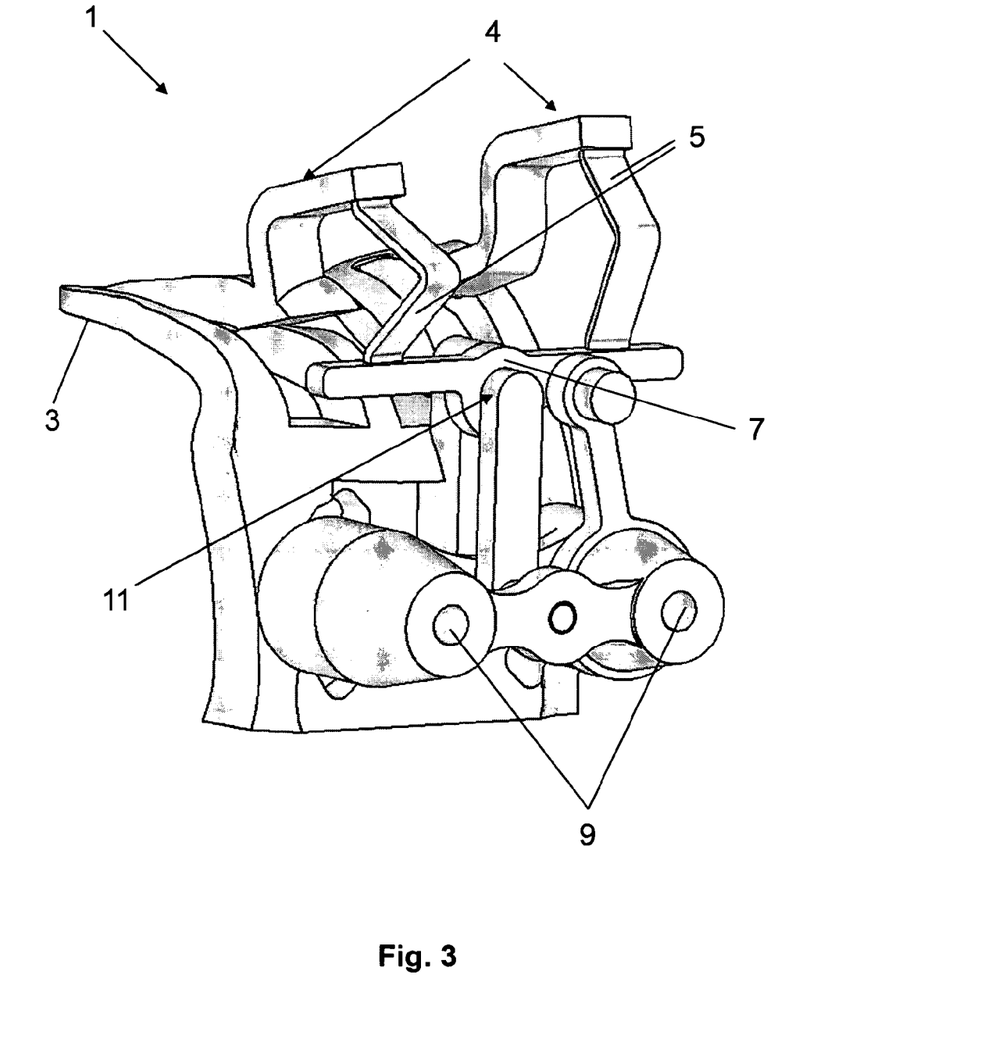
FIG. 3 is a schematic view of a third embodiment of an adaptable surgical guide according to the present invention.

FIG. 3 is a schematic view of yet another feedback device for use with a surgical guide 1 according to the present invention in a third embodiment. The third embodiment can be obtained by providing an elastic deformable element 5 between two known surfaces of the reference element 3 and the contact element 4. The reference element 3 has a surface that is patient specific, i.e. has the negative shape of a part of the patient's anatomy. The relative distance between these surfaces, which translates to a force created on the elastic deformable element 5, describes a way to measure force between two anatomic structures to aid in surgical planning. This feedback can be used to adapt the functional guidance elements 9 to the anatomy. For example, the force difference between medial and lateral knee condyles is measured by the guide to properly balance ligament tension with the resulting cut and implant position. While the illustration demonstrates correction through rotation, it is also possible to provide other paths or trajectories using other physical elements such as gears (seen in FIG. 4), hinges, screws etc. or by using an electronic function which then gives a resulting position of the functional guidance element 9. The guidance element 9 is shown as a drill guide with two holes for the guidance of drills. However the guidance element could be any type of guide for invasive operations such as a cutting guide for surgical interventions.

In an alternative embodiment of the present invention the functional guidance element can be locked in its final (intra-operative) position by means of any suitable locking means, e.g. that prevents rotation about the pivot.

Figure 4:
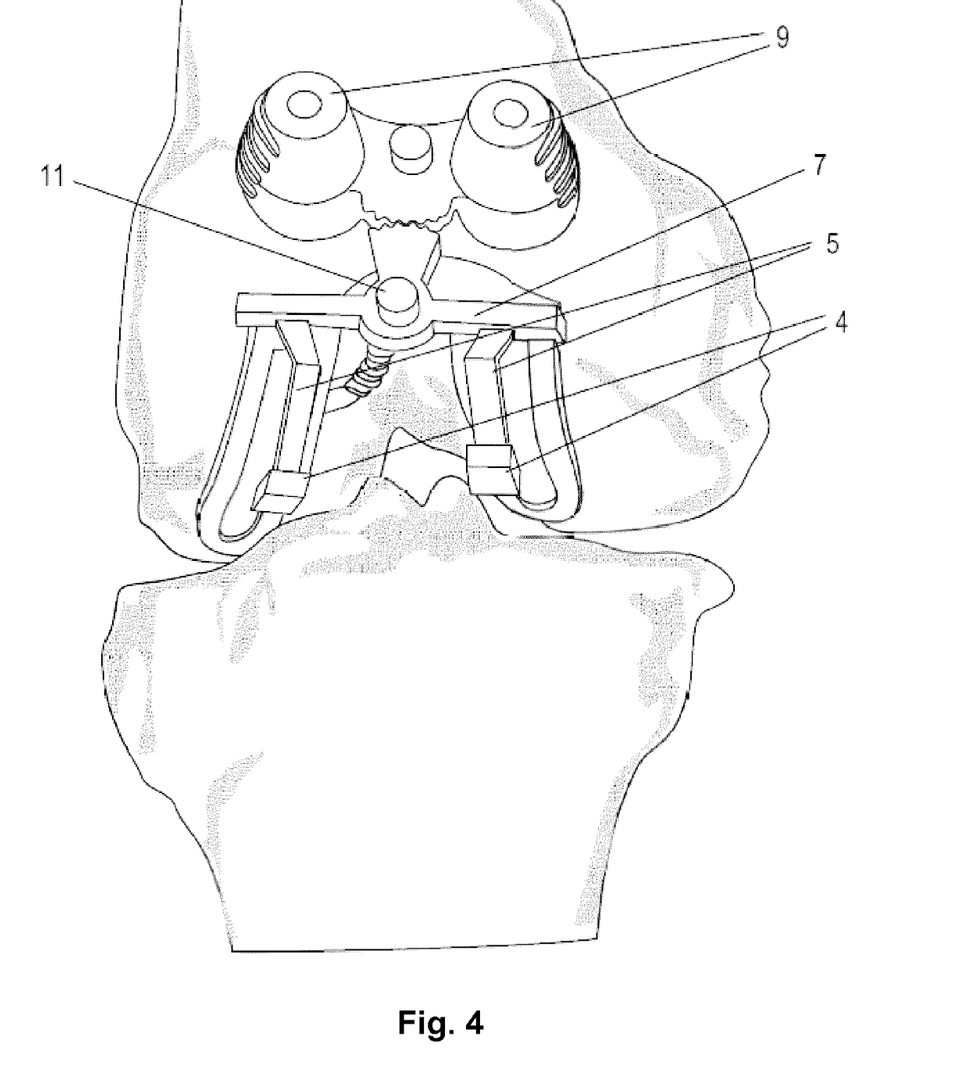
FIG. 4 shows the intra-operative position of the guide according to FIG. 3.

An important innovation of this guide is that it has a force feedback derived from the intra-operative anatomical position of anatomical elements, e.g. the knee condyles. The operation of the guide will be described with reference to FIGS. 3, 4 and 5. FIG. 4 shows the position of the guide intra-operatively. The contact elements 4 are in position and the angle between femur and tibia mechanical axis causes the angle of the guidance element 9 to change by rotation about the pivot 11—see FIG. 5. The guide device not only measures any difference between the positions of the condyles but also exerts forces on them so that they are placed in a more balanced anatomical position. Force feedback overcomes a number of problems with the current guide designs. Since soft tissue forces are not taken into account with the pre-operative planning, surgical plans are made based on skeletal mechanical alignment. Soft tissue balancing, and therefore force balancing, is not possible with static or manually adjustable guides and surgeons must change their surgical philosophy to mechanical alignment if they use these guides and surgical plans. By introducing a force measurement device, e.g. with force feedback, intra-operative soft tissue forces can be calculated by measuring their effects on the skeletal intra-articulating forces or these can also be balanced.

Figure 5:
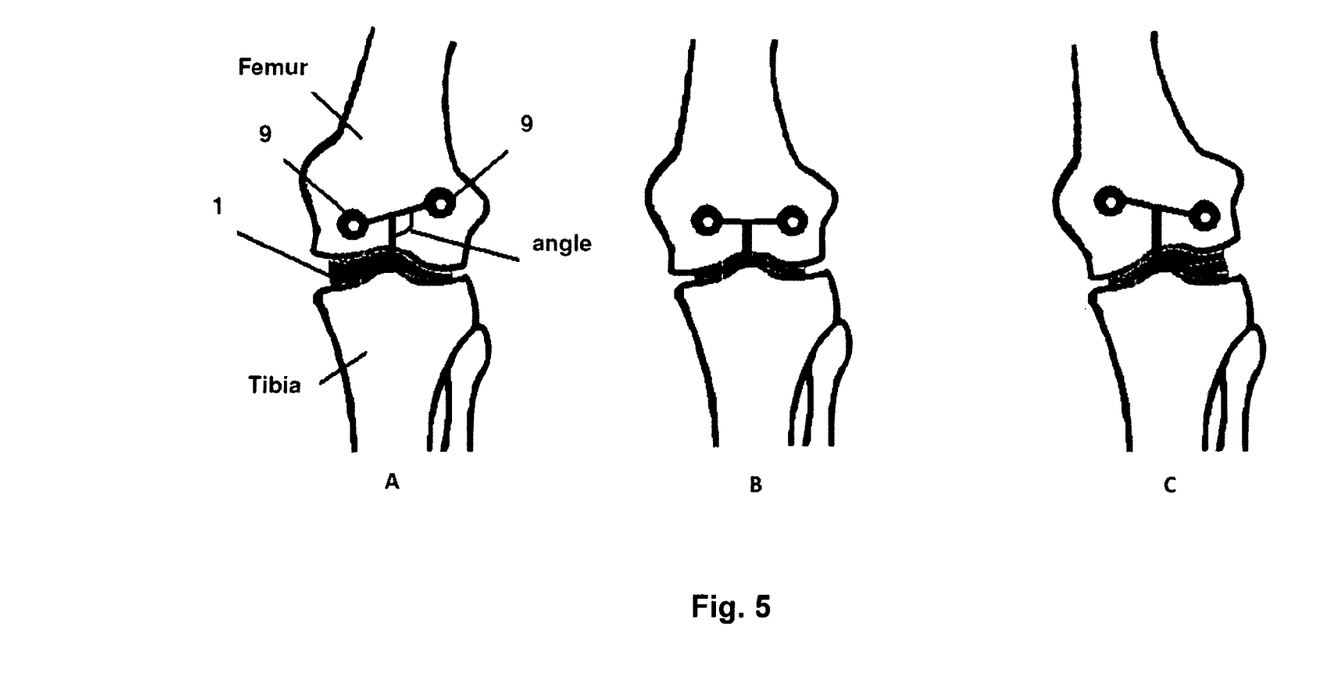
FIG. 5 illustrates the intra-operative function of the guide of FIG. 3

This measurement can be achieved using spring loaded surfaces or embedded strain gauges. These measurement devices are attached between the joint's contact surfaces. Spring loaded surfaces 4 can be attached to the functional guidance elements 9 like cut planes or drill holes so that intra-operative soft tissue measurements directly affect the surgical plan. The spring constant of the elastic element 5 can be varied based on patient's anatomy and expected force. Linking gear ratios or pivot or hinge placement 11 also provide methods to vary the functional guidance of element 9 to make them patient specific. Strain gauges as elastic elements 5 would provide a measurement read-out and the guides 1 would then be manually adjusted to accommodate for the force.

An anatomically matched reference element 3 of a known region and position is provided. Reference elements 3 can be used on two different anatomic surfaces, or between given device and an anatomic surface.

A spring providing resistance between two surface positions can be provided as elastic element 5. The change in the elastic deformable element 5 can be translated into force calculations. A force indicator (not shown) can be provided which provides a read-out of the force created between the two surfaces. This force measurement can be used as input to the transduction function.

The relative forces created by the elastic deformable elements 5 act on a transduction function part 7 which then moves the functional guidance element 9.

The guidance elements 9 for the surgical procedure can be described by cut planes, pin holes, or a number of other surgical guiding elements.

Although FIG. 3 has been described with reference to using a feedback device according to FIG. 2, any feedback device may be incorporated into a patient specific reference element 3 of the type shown in FIG. 3. Hence the feedback device of FIG. 1A, 1B, or 1C, may be included into a reference element as shown in FIG. 3 either alone or in combination.

Although FIGS. 1D and E have been described with reference to using a feedback device according to FIG. 1C, any feedback device may be incorporated into a patient specific reference element 3 of the type shown in FIG. 1D or E. Hence the feedback device of FIG. 1A, or 1B, or 2 or 3 may be included into a reference element as shown in FIG. 1D and FIG. 1E either alone or in combination.

Figure 6:
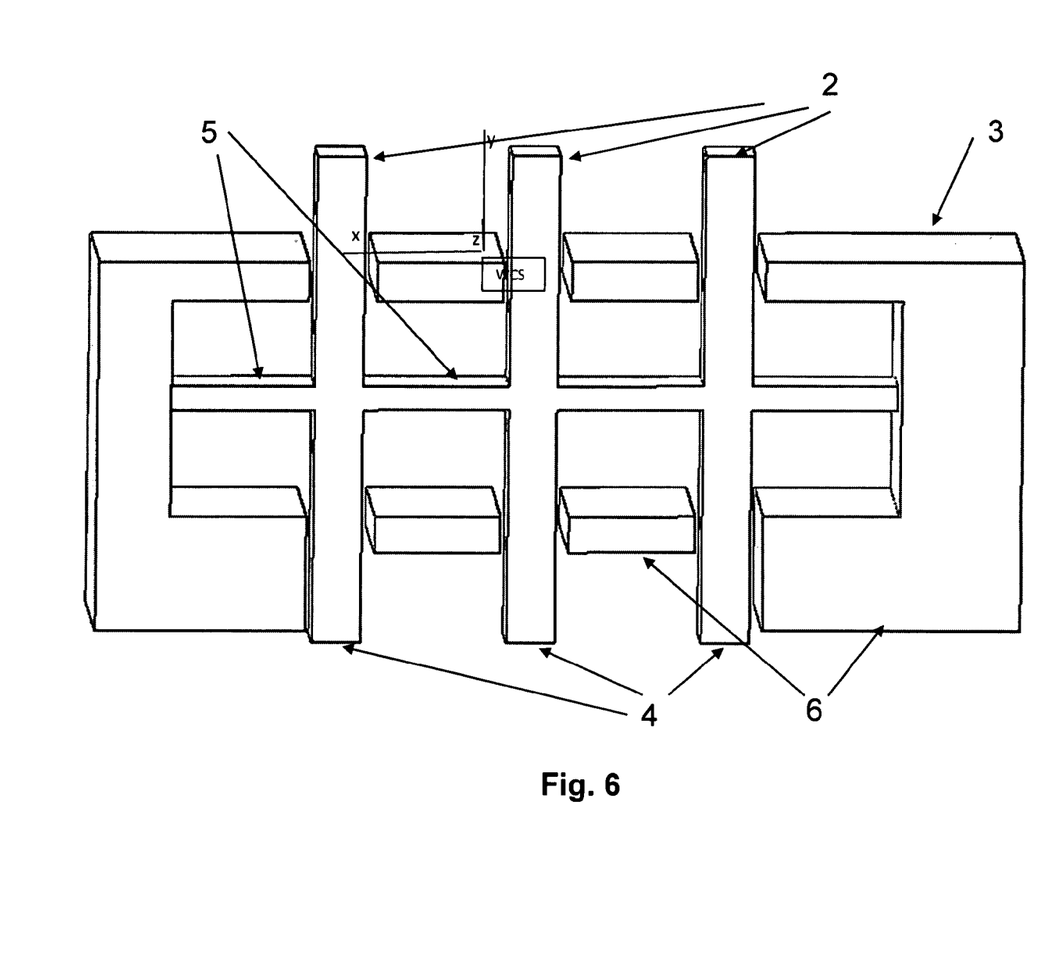
FIG. 6 is a schematic view of a fourth embodiment of an adaptable surgical guide according to the present invention that can be an alternative to any embodiment shown in FIGS. 1A-C.

FIG. 6 shows a further embodiment of the present invention. This embodiment may be used as an alternative to any of the embodiments described above such as those of FIGS. 1A, B, C. In this embodiment neither the reference element 3 nor the contact elements 4 are necessarily patient specific, i.e. has the negative shape of a part of the patient's anatomy. Instead the contact elements 4 are formed as pins all of the same length. However when the guide 1 is applied to the patient anatomy the pins move different amounts with reference to the second reference element surface 6 and indicators 2 will shows different lengths with respect to first reference element surface 3. Markings can be placed on the pins in a patient specific manner so that when the guide 1 is in the correct position, the markings give a visual feedback to this effect. Such markings can be introduced by additive manufacturing methods, e.g. layered manufacturing techniques sometimes called rapid prototyping manufacture. Also the contact elements 4 are connected together by a series of elastic elements 5 rather than being driven by only one elastic element 5. This may result in this guide being less accurate than the previous embodiments but easier to fabricate and it can be more compact.

Any of the above feedback devices and/or guides can be made by layered manufacturing techniques such as rapid prototyping techniques and additive manufacturing. This approach provides a cost effective manufacturing technology as the different reference elements, contact elements, guiding elements and elastic elements can be manufactured in one build, so that large amounts of them with complicated shapes can be integrated in the design of 1 specific guide. However the invention does not excluded that also components manufactured with other technologies can be assembled for instance to realise the transducer function.

Additive Manufacturing (AM) can be defined as a group of techniques used to quickly fabricate a scale model of an object typically using three-dimensional (3-D) computer aided design (CAD) data of the object. Currently, a multitude of Additive Manufacturing techniques is available, including stereo lithography (SLA), Selective Laser Sintering (SLS), Fused Deposition Modelling (FDM), foil-based techniques, etc. Stereo lithography, presently the most common AM technique, utilizes a vat of liquid photopolymer "resin" to build an object a layer at a time. On each layer, an electromagnetic ray, e.g. one or several laser beams which are computer-controlled, traces a specific pattern on the surface of the liquid resin that is defined by the two-dimensional cross-sections of the object to be formed. Exposure to the electromagnetic ray cures, or, solidifies the pattern traced on the resin and adheres it to the layer below. After a coat had been polymerized, the platform descends by a single layer thickness and a subsequent layer pattern is traced, adhering to the previous layer. A complete 3-D object is formed by this process.

Selective laser sintering (SLS) uses a high power laser or another focused heat source to sinter or weld small particles of plastic, metal, or ceramic powders into a mass representing the 3-dimensional object to be formed.

Fused deposition modelling (FDM) and related techniques make use of a temporary transition from a solid material to a liquid state, usually due to heating. The material is driven through an extrusion nozzle in a controlled way and deposited in the required place as described among others in U.S. Pat. No. 5,141,680.

Foil-based techniques fix coats to one another by means of gluing or photo polymerization or other techniques and cut the object from these coats or polymerize the object. Such a technique is described in U.S. Pat. No. 5,192,539.

Typically AM techniques start from a digital representation of the 3-D object to be formed. Generally, the digital is sliced into a series of cross-sectional layers which can be overlaid to form the object as a whole. The AM apparatus uses this data for building the object on a layer-by-layer basis. The cross-sectional data representing the layer data of the 3-D object may be generated using a computer system and computer aided design and manufacturing (CAD/CAM) software.

A selective laser sintering (SLS) apparatus is particularly preferred for the manufacture of the surface that is the negative form of a body part (as well as its support) from a computer model. It should be understood however, that various types of additive manufacturing and tooling may be used for accurately fabricating these surfaces and supports including, but not limited to, stereolithography (SLA), Fused Deposition Modeling (FDM) or milling.

The support for such a surface may be manufactured in different materials. Preferably, only materials that are biocompatible with the human body are taken into account. In the case SLS is used as a AM technique, the support for the surface may be fabricated from a polyamide such as PA 2200 as supplied by EOS, Munich, Germany or Duraform PA from 3D Systems, South Caroline, USA, or any other material known by those skilled in the art may also be used.

The guides of the present invention may be made using an image based method. Optionally they may be generated by additive or layered manufacturing, e.g. rapid prototyping manufacturing techniques directly from medical images of the patient such as optical, MRI, PET-scan, CT-scan images or Ultrasound images from which a surface can be generated, e.g. by segmentation. Patient specific surfaces (i.e. having the negative shape of a part of the patient's anatomy) can be produced by this method as well as patient specific markings on the indicators 2.

Other parts of the guides 1 such as the reference element 3 or the guidance element(s) 9 can also be created by additive or layered manufacturing, e.g. rapid prototyping manufacturing techniques using medical images of the patient such as optical, MRI, PET-scan, CT-scan images or Ultrasound images as a guide. For example, a guidance element 9 can be introduced into images and subsequently can be manufactured with an additive or layered manufacturing technique such as Rapid Prototyping or other additive fabrication technologies or with classic CNC technologies.

The present invention includes for any of the embodiments that image based techniques may be used to create all or part of the guides according to embodiments of the present invention. A scanner such as an optical, CT-San, MRI, PET, X-ray, Ultrasound imaging device may be used to generate a digital 3D geometry of the relevant shape, e.g. one or more of the patient specific elements as obtained by scanning the relevant body part. The image can be in the form of a point cloud, a solid surface consisting of triangles or any other format for recording and storing a 3D geometry. Another way of obtaining the required geometry is to manually make a plaster cast of the body part such as limb and to capture the shape of the cast by any suitable technique, e.g. scanning. Alternatively, a positive made from the cast can be scanned.

The geometry of the body part determined can be digitally imported into a computer program and may be converted using algorithms known from the field of CAD/CAM technology to produce a 3D computer model of a relevant surface. A computer program such as 3-Matic™ as supplied by Materialise N.V., Leuven, Belgium, may be used for constructing this 3D model. This geometry data can be used immediately in the computer program or stored in a digital file.

Once the 3D model of a patient specific surface (i.e. having the negative shape of a part of the patient's anatomy) is constructed, it may be manipulated manually, semi-automatically or automatically to design a 3D model of the relevant guide. These manipulations may include one or more of the following processes but are not limited to:

1. Scaling the geometry smaller or larger along certain axis.
2. Giving the geometry a thickness that can be varied throughout the part.
3. In creating hollow volumes inside this thickness.
4. Adding new surface shapes in certain parts, such as local elevations.
5. Adding predetermined 3D elements from a database system (E).
6. Integrating the interventions made into an optimal shape.
7. Adding attachment features that enable the attachment of straps or other means to fasten device to the person for whom it is designed.
8. Adding holes or other features.

A preferred method for performing these actions uses a computer program such a 3-matic as supplied by Materialise N.V., Leuven, Belgium.

A data base library of one or more 3D models of relevant structures or their mathematical representations may then be used to incorporate at least one functional structure into the 3D model of the device, e.g. a guidance element 9, a contact element 4, or a reference element 3 may be introduced. The elements in the library may be selected manually or automatically from the database by their pre-determined properties, such as their physical dimensions, their appearance or their mechanical properties. It is to be understood that the dimensions and values regarding the performance of all such imported structures available in the library may be scaled in any dimension to obtain the preferred or expected mechanical properties and performance. Functions representing them and their performance are preferably stored in this database so that they can be called up when required, automatically or manually by the user, and integrated into the 3D design using the design software. Specific structures may be called from the library or all structures matching certain performance parameters for the user to select for a particular location and purpose may be called. More than one structure can be selected by the library system to give certain areas of the device specific properties.

Figure 7:
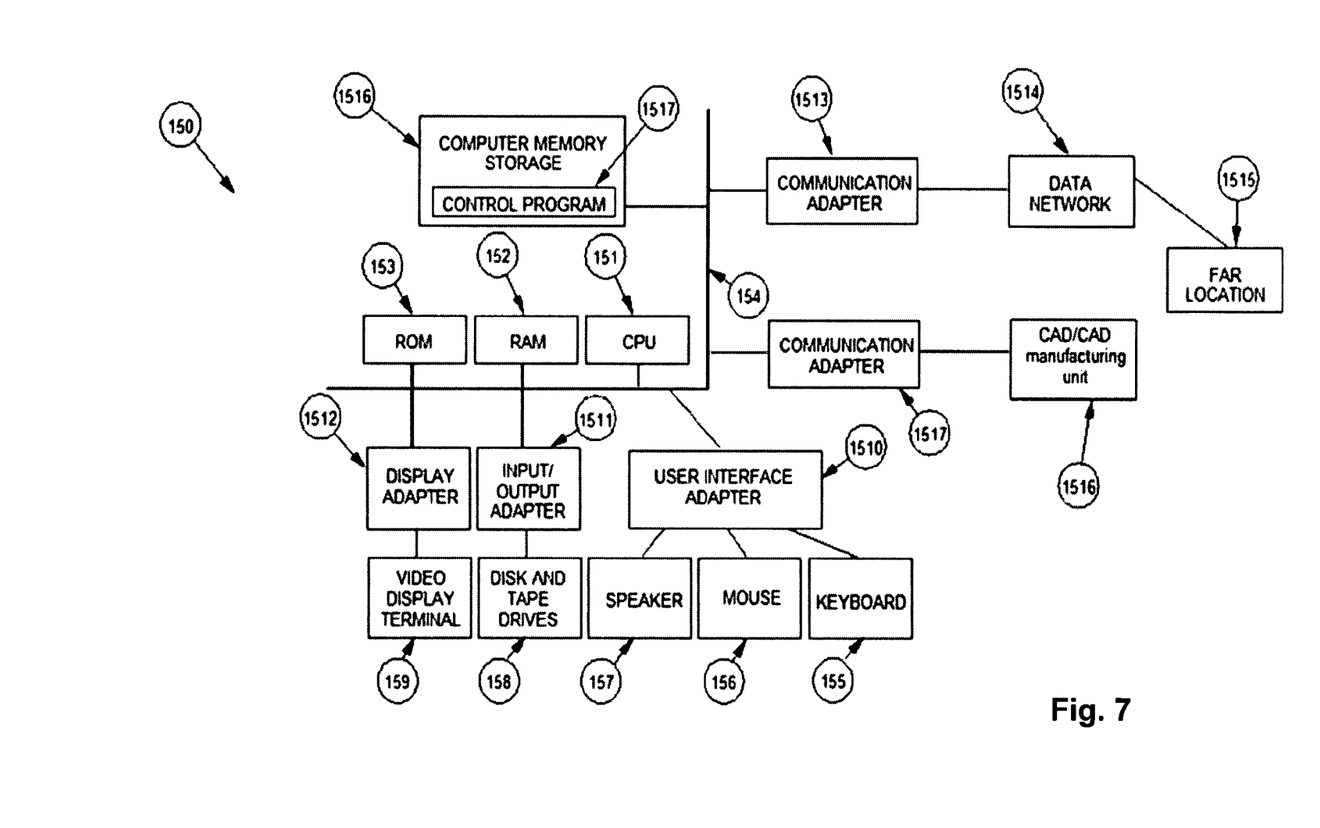
FIG. 7 is a schematic representation of a computer system according to the present invention.

FIG. 7 is a schematic representation of a computing system which can be utilized with the methods and in a system according to the present invention including computer programs such as 3-Matic™ as supplied by Materialise N.V., Leuven, Belgium. A computer 150 is depicted which may include a video display terminal 159, a data input means such as a keyboard 155, and a graphic user interface indicating means such as a mouse 156. Computer 150 may be implemented as a general purpose computer, e.g. a UNIX workstation or a personal computer.

Computer 150 includes a Central Processing Unit ("CPU") 151, such as a conventional microprocessor of which a Pentium processor supplied by Intel Corp. USA is only an example, and a number of other units interconnected via bus system 154. The bus system 154 may be any suitable bus system—FIG. 7 is only schematic. The computer 150 includes at least one memory. Memory may include any of a variety of data storage devices known to the skilled person such as random-access memory ("RAM"), read-only memory ("ROM"), non-volatile read/write memory such as a hard disc as known to the skilled person. For example, computer 150 may further include random-access memory ("RAM") 152, read-only memory ("ROM") 153, as well as a display adapter 1512 for connecting system bus 154 to a video display terminal 159, and an optional input/output (I/O) adapter 1511 for connecting peripheral devices (e.g., disk and tape drives 158) to system bus 154. Video display terminal 159 can be the visual output of computer 150, which can be any suitable display device such as a CRT-based video display well-known in the art of computer hardware. However, with a desk-top computer, a portable or a notebook-based computer, video display terminal 159 can be replaced with a LCD-based or a gas plasma-based flat-panel display. Computer 150 further includes user interface adapter 1510 for connecting a keyboard 155, mouse 156, optional speaker 157. The relevant data describing the 3-D object to be formed may be input directly into the computer using the keyboard 155 or from storage devices such as 158, after which a processor carries out a method in accordance with the present invention. The results of the method may be transmitted to a further near or remote location, e.g. a CAD/CAM processing facility to manufacture the template in accordance with the details provided by computer 150.

A CAD/CAM manufacturing unit 1516 may also be connected via a communications adapter 1517 to bus 154 connecting computer 150 to a data network such as the Internet, an Intranet a Local or Wide Area network (LAN or WAN) or a CAN. The manufacturing unit 1516 may receive an output value or support descriptor file directly from computer 150 running a computer program for support design in accordance with the present invention or a value or descriptor file derived from such an output of computer 150. Alternatively, the unit 1516 may receive the relevant design data indirectly on a suitable signal storage medium such as a diskette, a replaceable hard disc, an optical storage device such as a CD-ROM or DVD-ROM, a magnetic tape or similar.

Computer 150 also includes a graphical user interface that resides within machine-readable media to direct the operation of computer 150. Any suitable machine-readable media may retain the graphical user interface, such as a random access memory (RAM) 152, a read-only memory (ROM) 153, a magnetic diskette, magnetic tape, or optical disk (the last three being located in disk and tape drives 158). Any suitable operating system and associated graphical user interface (e.g., Microsoft Windows, Linux) may direct CPU 151. In addition, computer 150 includes a control program 1517 that resides within computer memory storage 1516. Control program 1517 contains instructions that when executed on CPU 151 allow the computer 150 to carry out the operations described with respect to any of the methods of the present invention.

Those skilled in the art will appreciate that the hardware represented in FIG. 7 may vary for specific applications. For example, other peripheral devices such as optical disk media, audio adapters, or chip programming devices, such as PAL or EPROM programming devices well-known in the art of computer hardware, and the like may be utilized in addition to or in place of the hardware already described.

In the example depicted in FIG. 7, the computer program product for carrying out a method of the present invention can reside in any suitable memory. However, it is important that while the present invention has been, and will continue to be, that those skilled in the art will appreciate that the mechanisms of the present invention are capable of being distributed as a computer program product in a variety of forms, and that the present invention applies equally regardless of the particular type of signal bearing media used to actually carry out the distribution. Examples of computer readable signal bearing media include: recordable type media such as floppy disks and CD ROMs and transmission type media such as digital and analogue communication links.

Accordingly, the present invention also includes a software product which when executed on a suitable computing device carries out any of the methods of the present invention. Suitable software can be obtained by programming in a suitable high level language such as C and compiling on a suitable compiler for the target computer processor.

While the invention has been shown and described with reference to preferred embodiments, it will be understood by those skilled in the art that various changes or modifications in form and detail may be made without departing from the scope and spirit of this invention.

The invention claimed is:

1. A therapeutic, diagnostic or surgical guide adapted for intra-operative positioning on a patient, comprising:
   a first reference element comprising a rigid structure shaped to fit a specific area of the patient;
   a first contact element elastically mounted with respect to the reference element by means of a first elastic element; and
   a first guidance element attached to the first reference element,
   wherein positioning the guide on the patient causes a deformation of the first elastic element.

2. A therapeutic diagnostic or surgical guide according to claim 1, wherein the first guidance element is adaptively attached to the first reference element, so that deformation of the first elastic element causes an adaptation of the first guidance element.

3. A therapeutic, diagnostic or surgical guide according claim 1, wherein the guide comprises a second contact element.

4. A therapeutic, diagnostic or surgical guide according to claim 3, wherein the first and second contact elements define points adapted to fit a specific targeted area the patient.

5. A therapeutic, diagnostic or surgical guide according to claim 1, wherein the first elastic element is chosen from the group consisting of a strain gauge, a spring, rubber, a deformable foam, and an inflatable cushion.

6. A therapeutic, diagnostic or surgical guide according to claim 1, wherein the guide comprises a second reference element attached to or integral with the first reference element.

7. A therapeutic, diagnostic or surgical guide according to claim 1, further comprising a force feedback element in operative contact with the first guidance element.

8. A therapeutic, diagnostic or surgical guide according to claim 7, wherein the force feedback element comprises a transducer element attached to the first elastic element and in operative contact with the first guidance element.

9. A therapeutic, diagnostic or surgical guide according to claim 7, wherein the force feedback element comprises an actuator element attached to the first elastic element.

10. A therapeutic, diagnostic or surgical guide according to claim 1, further comprising a means to lock the first guidance element.

11. A method of making a guide according to claim 1, the method including an additive manufacturing technique including at least one of rapid prototyping and layered manufacture.

12. A medical template that provides feedback comprising:
    a reference element;

a patient-specific element elastically coupled to the reference element and shaped to fit a specific area of a patient; and an indicator actuated by the patient-specific element for providing feedback relating to a position of the patient-specific element relative to the patient, the feedback indicating whether the template is in a correct position.

13. The template of claim 12, wherein the feedback includes at least one of visual feedback and force feedback.

14. The template of claim 12, wherein the patient-specific element is a contact element comprising a point or surface and wherein the patient-specific element is made flexible by means of an elastic element.

15. A template to claim 14, wherein the elastic element is chosen from the group consisting of a strain gauge, a spring, rubber, a deformable foam, and an inflatable cushion.

16. A method of making a template according to claim 12, the method including an additive manufacturing technique including at least one of rapid prototyping and layered manufacture.

17. The template of claim 12, wherein said template is a therapeutic, diagnostic or surgical template.

18. The template of claim 12, further comprising a guidance element, wherein the indicator is configured to actuate the guidance element.

* * * * *